United States Patent [19]

Ella

[11] Patent Number: 4,888,958
[45] Date of Patent: Dec. 26, 1989

[54] COOLING APPARATUS FOR LOW AIR LOSS THERAPY BEDS

[76] Inventor: Gregory R. Ella, 225 S. Jackson, Denver, Colo. 80209

[21] Appl. No.: 277,792

[22] Filed: Nov. 30, 1988

[51] Int. Cl.$^4$ ............................................. F75D 15/00
[52] U.S. Cl. .......................................... 62/237; 5/423; 5/508; 62/261; 98/38.1; 285/179
[58] Field of Search ................... 62/237, 261; 98/38.1, 98/38.9, DIG. 7, 89; 5/423, 508; 285/179

[56] References Cited

U.S. PATENT DOCUMENTS

| | | | |
|---|---|---|---|
| 2,105,108 | 1/1938 | Crosley, Jr. | 62/261 |
| 2,461,432 | 2/1949 | Mitchell | 5/284 |
| 2,477,619 | 8/1949 | Kennedy | 98/38.1 |
| 2,502,263 | 3/1950 | Lewis | 62/261 |
| 2,620,636 | 12/1952 | Stanton | 62/237 X |
| 2,998,817 | 9/1961 | Armstrong | 128/33 |
| 3,266,064 | 8/1966 | Figman | 5/347 |
| 3,444,922 | 6/1969 | Dingman | 5/423 X |
| 3,486,177 | 12/1969 | Marshack | 5/347 |
| 3,928,876 | 12/1975 | Starr | 5/284 |
| 4,006,604 | 2/1977 | Seff | 62/261 |
| 4,197,837 | 4/1980 | Tringali et al. | 128/33 |
| 4,425,676 | 1/1984 | Crane | 5/450 |
| 4,525,885 | 7/1985 | Hunt et al. | 5/453 |
| 4,638,519 | 1/1987 | Hess | 5/455 |

Primary Examiner—William E. Tapolcai
Attorney, Agent, or Firm—John R. Flanagan

[57] ABSTRACT

A cooling appartus for a low air loss therapy bed includes a portable self-contained cooling unit for generating a flow of cool air and a flexible conduit connected to the cooling unit for routing the flow of cool air from the cooling unit. The cooling apparatus also includes an adapter releasably connected to the intake manifold of the bed and having a shroud for allowing passage of a flow of ambient air to the inlet of the manifold and second means coupled to conduit for communicating the flow cool air from said conduit to the inlet without obstructing ambient air flow to the inlet.

14 Claims, 2 Drawing Sheets

COOLING APPARATUS FOR LOW AIR LOSS THERAPY BEDS

BACKGROUND OF THE INVENTION

1. Field of the Invention

The present invention generally relates to low air loss therapy beds and, more particularly, is concerned with a cooling apparatus for lowering the operating temperature of such beds.

2. Description of the Prior Art

A low air loss therapy bed is a specialized piece of medical equipment for bedridden patients. Its primary function is to provide a low pressure support environment conducive to the prevention and treatment of decubitus ulcers (bed sores) and the healing of skin grafts and burns. One conventional design is illustrated and disclosed in U.S. Pat. No. 4,525,885 to Hunt et al assigned to Mediscus Products Limited.

In the one conventional design of the Hunt et al patent, the low air loss therapy bed includes a number of air sacs for supporting the patient, a frame to support the air sacs, an air blower to inflate the air sacs, a pressure control system for regulating the blower, and a bed-posture control system. The air sacs are composed of a breathable fabric such as polyurethane coated nylon or a material sold under the Gore-Tex trademark. Fresh ambient room air is continually drawn in by the blower and supplied to the sacs, where the air circulates and exits through the fabric (and in some beds also through exit valves).

Further, the bed has a built-in heating system. However, up to the present time, one important shortcoming has been that the bed does not have a system for cooling the air. Typically, the bed runs 10 degrees F. above room temperature even with the heating system off. There are instances when a cooling system would be highly desirable. One instance is where ambient air temperature results in an undesirably high bed operating temperature, such as in a non-air conditioned facility in a warm climate in the summertime. Another instance is in the case of a febrile patient where the medical care provider wishes to reduce the temperature of the patient's immediate environment.

In view of the aforementioned shortcoming, it has been perceived by the inventor herein that a need exists for a way to reduce the operating temperature of such bed.

SUMMARY OF THE INVENTION

The present invention provides a low air loss bed cooling apparatus designed to overcome the above-cited shortcoming and to satisfy the aforementioned needs. Advantageously, the cooling apparatus of the present invention includes a portable self-contained cooling unit and an adapter for releasably connecting the unit to an inlet of the therapy bed without obstructing or impeding ambient room air flow into the inlet of the bed. The unit can be used to reduce the bed operating temperature brought about by elevated ambient air temperatures or merely arising from normal circulation of air through the bed. The cooling apparatus advantageously provides a means to positively regulate or reduce the operating temperature of the bed.

Accordingly, the present invention is directed to a cooling apparatus for use with a low air loss therapy bed having an intake manifold with an air inlet. The cooling apparatus comprises: (a) a cooling unit for generating a flow of cool air; (b) a flexible conduit connected to the cooling unit for routing the flow of cool air from the cooling unit; and (c) an adapter releasably connectible to the intake manifold of the bed and having first means for allowing passage of a flow of ambient air to the inlet of the manifold and second means coupled to the conduit for communicating the flow of cool air from the conduit to the inlet without obstructing or impeding ambient air flow to the inlet via the first means.

The present invention is also directed to the cooling unit for generating the flow of cool air for cooling the low air loss therapy bed. The cooling unit comprises: (a) a mobile housing having a plurality of interconnected exterior walls and an intermediate interior wall which together define a pair of separate side-by-side hollow compartments having respective inlets and outlets by which ambient air can enter and exit the separate housing compartments; (b) air flow generating means disposed in each of the respective housing compartments and being operable for inducing separate flows of ambient air through the compartments from the inlets to the outlets thereof; (c) heat exchanging means disposed in each of the respective housing compartments across the respective separate flows of ambient air through the compartments, the heat exchanging means being connected in flow communication with one another; and (d) refrigerant pumping means disposed in the housing and connected in flow communication with the heat exchanging means in each of the compartments for pumping a refrigerant in vapor state to a first one of the heat exchanging means where heat is released by the refrigerant to the air flow passing across the first heat exchanging means causing condensing of the refrigerant to a high pressure liquid state and for receiving the refrigerant in vapor state from a second one of the heat exchanging means where heat is released to the refrigerant by the air flow passing across the second heat exchanging means as a result of expansion of the refrigerant from its high pressure liquid to a low pressure vapor state at the second heat exchanging means. The release of heat by the air flow passing across the second heat exchanging means produces a flow of cool air from the outlet of the corresponding housing compartment.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the course of the following detailed description, reference will be made to the attached drawings in which.

DETAILED DESCRIPTION OF THE INVENTION

Figure 1:
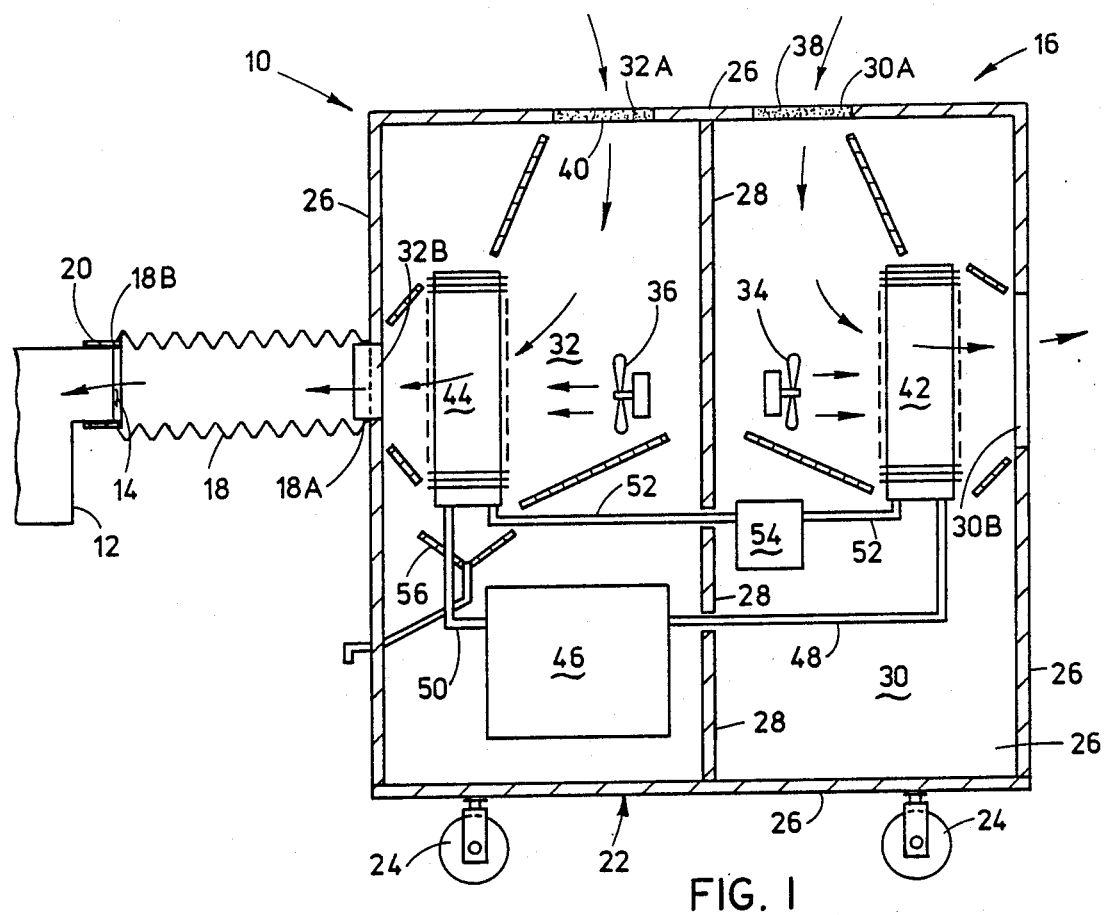
FIG. 1 is a schematic view of a cooling apparatus of the present invention coupled to an air intake manifold of a conventional therapy bed.

Referring now to the drawings, and particularly to FIG. 1, there is shown a cooling apparatus, generally designated by the numeral 10, which is constructed in accordance with the principles of the present invention. The cooling apparatus 10 is adapted for use with a low air loss therapy bed (not shown) such as the one illustrated and described in U.S. Pat. No. 4,525,885, the disclosure of which is incorporated herein by reference. As illustrated in FIG. 1, the cooling apparatus 10 is connected to an intake manifold 12 of the bed in flow communication with an ambient air inlet 14 defined in the manifold.

For the therapy bed to function properly, a blower (not shown) in the bed must continually draw in fresh ambient room air through the air inlet 14 of the intake manifold 12 and supply the necessary low pressure air to a plurality of air sacs (not shown) to maintain the sacs in an inflated condition for supporting the patient on the bed. Ambient air is circulated through the air sacs before exiting through their fabric. Neither the bed nor its operation need be described herein in any greater detail for a clear and thorough understanding of the cooling apparatus 10 of the present invention. For a gaining a greater understanding of the operation of the bed, attention is directed to the above-cited patent.

As seen in FIG. 1, in its basic components the cooling apparatus 10 includes a portable self-contained cooling unit 16, a flexible conduit 18 and an adapter 20. The cooling unit 16 is operable for generating a flow of cool air. The flexible conduit 18 is provided for connection at one end 18A to the cooling unit 16 for routing cool air from the unit. The adapter 20 is configured for releasably connecting the opposite end 18B of the conduit 18 to the intake manifold 12 of the therapy bed for communicating the cool air from the conduit 18 to inlet 14 of the bed without obstructing or impeding concurrent flow of ambient room air through the intake manifold inlet 14 of the bed.

More particularly, the cooling unit 16 of the apparatus 10 for generating the flow of cool air is a portable self-contained unit having a housing 22 supported b a plurality of ground-engaging wheels 24 which renders the unit 16 mobile and capable of being moved about easily. The housing 22 is of generally rectangular box-shape and has a plurality of interconnected exterior walls 26 and an intermediate vertically-extending interior wall 28 which define a pair of separate side-by-side hollow compartments 30, 32. The compartments 30, 32 have respective inlets 30A, 32A and outlets 30B, 32B by which ambient room air can enter and exit the separate compartments 30, 32 of the housing 22.

The cooling unit 16 of the apparatus 10 also includes respective air flow generating means in the form of blowers 34, 36 disposed in the respective housing compartments 30, 32. The blowers 34, 36 are operable for drawing ambient air into the respective compartments 30, 32 of the housing 22 through filters 38, 40 disposed across the housing inlets 3OA, 32A. The cooling unit 16 further includes heat exchanging means in the form of a condenser 42 and an evaporator 44 disposed in the respective compartments 30, 32 across the paths of air flow induced by the blowers 34, 36. The air flow induced by the blower 34 exits the housing compartment outlet 30B after passing across the condenser 42, whereas the air flow induced by the blower 36 exits the housing compartment outlet 32B after passing across the evaporator 44.

The cooling unit 16 of the apparatus 10 further includes a refrigerant pumping means in the form of a compressor 46 disposed in the housing 22 and connected at its outlet by a flow line 48 (passing through the interior wall 28 of the housing 22) in flow communication with the inlet of the condensor 42 and at its inlet by a flow line 50 in flow communication with the outlet of the evaporator 44. The outlet of the condensor 42 is connected by a flow line 52 (also passing through the interior wall 28 of the housing 22) in flow communication with the inlet of the evaporator 44. An expansion valve (not shown) is disposed in the flow line 52 just upstream of the inlet of the evaporator 44. A reservoir-drier 54 is interposed in the flow line 52. A sump 56 is disposed below the evaporator 44 for collection of any moisture condensing on evaporator 44.

Briefly, the operation of the cooling unit 16 is as follows. The compressor 46 pumps vaporized refrigerant to the condenser 42 via flow line 48. At the condenser 42 the vaporized refrigerant loses heat to the air flow passing across the condenser 42 and condenses into a high pressure liquid. The air heated by the condenser 42 passes from the housing compartment 30 through the exit 30A and back into the atmosphere. The liquid refrigerant then flows in line 52 to the reservoir-drier 54 where trace moisture is removed from the refrigerant. Liquid refrigerant then flows on via flow line 52 to the evaporator 44. The expansion valve located at the inlet to the evaporator 44 causes the liquid refrigerant to undergo a pressure drop, causing it to absorb heat from the evaporator 44 and air flowing across the evaporator and vaporize. The refrigerant then flows as a vapor through the evaporator 44 and back to the compressor 46 via flow line 50 completing the circuit. Thus, heat is removed from the air flow passing across the evaporator 44, producing a flow of cool air at the outlet 32B of the housing compartment 32.

The cooling unit 16 of the apparatus 10 is thus operable for generating a flow of cool air. The elongated flexible conduit 18 of the apparatus 10 is connected at one end 18A to the housing compartment outlet 32B of the cooling unit 16 for routing the flow of cool air from the cooling unit 16. The adapter 20 of the apparatus 10 is configured for releasably connecting the opposite end 18B of the flexible conduit 18 to the intake manifold 12 of the therapy bed for communicating the flow of cool air from the conduit 18 to inlet 14 of the bed.

The adapter 20 is designed to interfit with the air intake manifold 12 of the bed for communicating and concentrating the flow of cool air about the inlet 14 of the manifold 12 without obstructing or impeding concurrent flow of ambient room air through the intake manifold inlet 14 of the bed for sustaining normal conventional operation of the bed as briefly described earlier. Thus, if the required flow of air being drawn into the bed by a blower (not shown) in the bed to sustain inflation of the air sacs is greater than the flow of cool air from the cooling unit 16, the difference is made up by ambient air drawn in the bed through the manifold 12 in an unobstructed manner directly from the room along a path which is separate from and, in effect, by-passes the cooling unit 16 and conduit 18.

Several embodiments of the adapter of the cooling apparatus 10 designed for accommodating coupling of the apparatus 10 to different conventional versions of low air loss therapy beds are shown in FIGS. 2–5. In the one embodiment of FIGS. 2 and 3, the adapter 20 is in the form of a hollow shroud 58 releasably connected to the intake manifold 12 of the bed by latching means such as toggle catches 60. The toggle catches 60 allow easy attachment or removal of the adapter 20 to or from the bed manifold 12. The major portion of the shroud 58 is spaced from the air inlet 14 of the intake manifold 12 so as to define an air flow chamber 62 therebetween communicating with the manifold air inlet 14. The shroud 58 also defines an opening 64 communicating with the air flow chamber 62 for entry of ambient air flow from the room into the chamber 62 and therefrom to the manifold inlet. The shroud 58 further has a cylindrical port 66 defined thereon by which the opposite end 18B of the flexible conduit 18 is coupled to the shroud 58 and air flow chamber 62 for communicating the flow of cool air from the cooling unit 16 and conduit 18 to the manifold inlet 14 without obstructing ambient air flow to the inlet through the opening 64. The cool air receiving port 66 is separate from the ambient air receiving opening 64.

Figure 2:
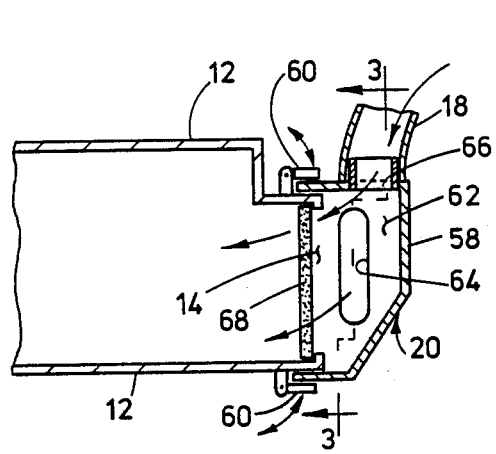
FIG. 2 is a side elevational schematic view of a first embodiment of an adapter of the cooling apparatus for coupling a cooling unit of the apparatus to an ambient air intake manifold of one version of a conventional therapy bed.
Figure 3:
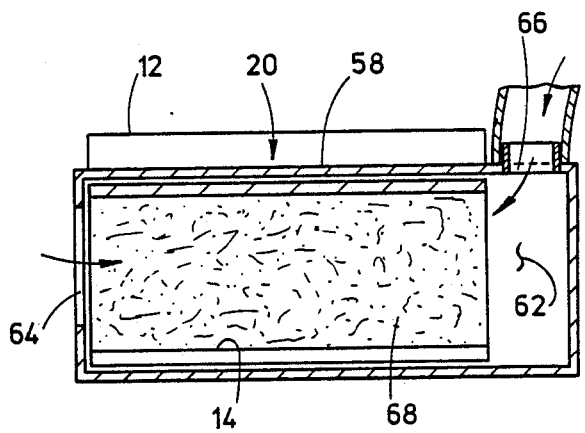
FIG. 3 is a vertical sectional view of the adapter taken along line 3—3 of FIG. 2.
Figure 4:
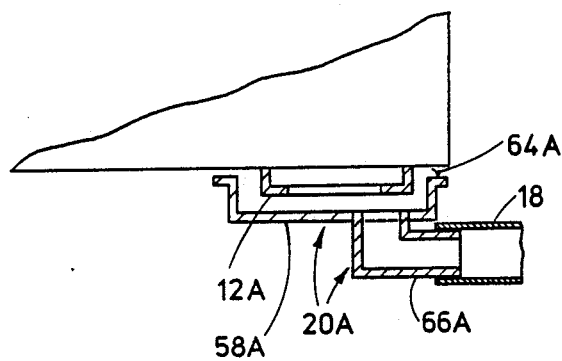
FIG. 4 is a side elevational schematic view of a second embodiment of an adapter of the cooling apparatus for coupling the cooling unit of the apparatus to an ambient air intake manifold of another version of the therapy bed.
Figure 5:
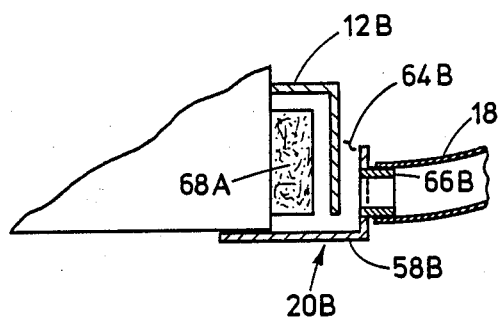
FIG. 5 is a side elevational schematic view of a third embodiment of an adapter of the cooling apparatus for coupling the cooling unit of the apparatus to an ambient air intake manifold of still another version of the therapy bed.

In the one embodiment of FIGS. 2 and 3, the ambient air receiving opening 64 of the adapter 20 is in the form of a hole defined through the shroud 58. In the respective embodiments of FIGS. 4 and 5 which have manifolds 12A and 12B somewhat modified in configuration from the manifold 12 in FIGS. 2 and 3, the respective ambient air receiving openings 64A, 64B of the adapters 20A, 20B are gaps defined between the manifolds 12A, 12B and the peripheries of the shrouds 58A, 58B. In both of the embodiments shown in FIGS. 2, 3 and 5, air filters 68, 68A are provided across the manifold inlets 14, 14A.

The cooling unit 16 uses the same type of electrical power source as the low air loss system of the therapy bed with which it is used. For example, universally-available conventional 110 volt, 60 Hz, single phase electrical power source can be used.

It is thought that the present invention and many of its attendant advantages will be understood from the foregoing description and it will be apparent that various changes may be made in the form, construction and arrangement of the parts thereof without departing from the spirit and scope of the invention or sacrificing all of its material advantages, the forms hereinbefore described being merely preferred or exemplary embodiments thereof.

Having thus described the invention, what is claimed is:

1. An apparatus for cooling a low air loss therapy bed having an intake manifold with an inlet, said apparatus comprising:
   (a) a cooling unit for generating a flow of cool air;
   (b) a flexible conduit connected to the cooling unit for routing the flow of cool air from said cooling unit; and
   (c) an adapter releasably connectible to the intake manifold of the bed and having first means for allowing passage of a flow of ambient air to the inlet of the manifold and second means coupled to said conduit for communicating the flow of cool air from said conduit to the inlet without obstructing ambient air flow to the inlet via said first means;
   (d) said first means of said adapter being a shroud releasably connectible to the manifold and spaced therefrom so as to define an air flow chamber therebetween communicating with the manifold inlet, said shroud also defining an opening communicating with said chamber for entry of ambient air flow into said chamber.

2. The apparatus as recited in claim 1, wherein said cooling unit is a portable self-contained unit.

3. The apparatus as recited in claim 1, wherein said second means of said adapter is a port defined on said shroud separate from said opening for entry of ambient air flow, said port communicating with said chamber and connected to said conduit for entry of cool air flow into said chamber.

4. The apparatus as recited in claim 1, wherein said opening of said adapter is a hole defined through said shroud.

5. The apparatus as recited in claim 1, wherein said opening of said adapter is gap defined between said shroud and the manifold.

6. The apparatus as recited in claim 1, wherein said cooling unit includes:
   a pair of separate side-by-side hollow compartments having respective inlets and outlets by which ambient air can enter and exit said separate compartments.

7. The apparatus as recited in claim 6, wherein said cooling unit further includes:
   air flow generating means disposed in each of said respective compartments and being operable for inducing separate flows of ambient air through said compartments from said inlets to said outlets thereof.

8. The apparatus as recited in claim 7, wherein each of said air flow generating means is a blower.

9. The apparatus as recited in claim 7, wherein said cooling unit further includes:
   heat exchanging means disposed in each of said respective compartments across the respective separate flows of ambient air through said compartments and being connected in flow communication with one another.

10. The apparatus as recited in claim 9, wherein one of said heat exchanging means is a condenser and the other is an evaporator.

11. The apparatus as recited in claim 9, wherein said cooling unit further includes:
    refrigerant pumping means connected in flow communication with said heat exchanging means in each of said compartments for pumping a refrigerant in vapor state to a first one of said heat exchanging means where heat is released by the refrigerant to the air flow passing across said first heat exchanging means causing condensing of the refrigerant to a high pressure liquid state and for receiving the refrigerant in vapor state from a second one of said heat exchanging means where heat is released to the refrigerant by the air flow passing across said second heat exchanging means as a result of expansion of the refrigerant from its high pressure liquid to a low pressure vapor state at said second heat exchanging means, said release of heat by the air flow passing across said second heat exchanging means producing a flow of cool air from said outlet of said corresponding compartment.

12. The apparatus as recited in claim 11, wherein said refrigerant pumping means is a compressor.

13. The apparatus as recited in claim 11 wherein said cooling unit is a portable self-contained unit.

14. The apparatus as recited in claim 11, wherein said second means of said adapter is a port defined on said shroud separate from said opening for entry of ambient air flow, said port communicating with said chamber and connected to said conduit for entry of cool air flow into said chamber.

* * * * *